US007556922B2

(12) United States Patent
Block et al.

(10) Patent No.: US 7,556,922 B2
(45) Date of Patent: Jul. 7, 2009

(54) MOTION RESOLVED MOLECULAR SEQUENCING

(75) Inventors: Steven M. Block, Redwood City, CA (US); William Greenleaf, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 51 days.

(21) Appl. No.: 11/726,513

(22) Filed: Mar. 21, 2007

(65) Prior Publication Data

US 2008/0020392 A1 Jan. 24, 2008

Related U.S. Application Data

(60) Provisional application No. 60/785,795, filed on Mar. 23, 2006.

(51) Int. Cl.
*C12Q 1/68* (2006.01)
(52) U.S. Cl. .......................................................... 435/6
(58) Field of Classification Search ........................ None
See application file for complete search history.

(56) References Cited

OTHER PUBLICATIONS

Shundrovsky et al. (Biophysical Journal, 2004, vol. 87, p. 3945-3953).*
Sanger et al. (PNAS, 1977, vol. 74, No. 12, p. 5463-5467).*
Shaevitz et al. (Nature, 2003, vol. 426(6967), p. 1-11).*
Kasas et al. (Biochemistry, 1997, vol. 36, No. 3, p. 461-468).*
Gosse et al. (Biophysical Journal, 2002, vol. 82, p. 3314-3329).*
Davenport et al. (Science, 2000, vol. 287, p. 2497-2500).*
Abbondanzieri et al., "Direct observation of base-pair stepping by RNA polymerase," Nature, 2005, 438 (7067):460-465.
Akeson et al., "Microsecond time-scale discrimination among polycytidylic acid, polyadenylic acid, and polyuridylic acid as homopolymers or as segments within single RNA molecules," Biophys. J, 1999, 77(6):3227-3233.
Braslavsky et al., "Sequence information can be obtained from single DNA molecules," Proc. Natl. Acad. Sci. USA, 2003, 100(7):3960-3964.
Greenleaf et al., "Passive all-optical force clamp for high-resolution laser trapping," Phys. Rev. Lett., 2005, 95(20):208102.
Herbert et al., "Sequence-resolved detection of pausing by single RNA polymerase molecules," Cell, 2006, 125(6):1083-1094.
Service, "Gene sequencing. The race for the $1000 genome," Science, 2006, 311(5767):1544-1546.
Shaevitz et al., "Backtracking by single RNA polymerase molecules observed at near-base-pair resolution," Nature, 2003, 426(6967):684-687.

* cited by examiner

*Primary Examiner*—Gary Benzion
*Assistant Examiner*—Stephanie K Mummert
(74) *Attorney, Agent, or Firm*—Bozicevic, Field & Francis LLP; Pamela J. Sherwood

(57) ABSTRACT

Methods are provided for determining the sequence of a polynucleotide by tracking the motion of a nucleotide-selective, processive enzyme along a template, in a reaction mixture that alters the enzyme movement in a base specific manner. The movement trace of the enzyme is collected, and arranged in temporal order. The enzyme movement traces are correlated with the reaction conditions, and from these characteristic signals, the nucleotide sequence is derived.

20 Claims, 6 Drawing Sheets

(1) Call all unique peaks  (2) Resolve any peak conflicts  (3) Call the highest traces

MOTION RESOLVED MOLECULAR SEQUENCING

GOVERNMENT RIGHTS

This invention was made with Government support under contract GM057035 awarded by the National Institutes of Health. The Government has certain rights in this invention.

BACKGROUND OF THE INVENTION

Polynucleotide sequencing is the process of determining the nucleotide order of a given DNA or RNA fragment. These methods were first used in the sequencing of fragments, then individual genes, and have now been applied to whole genomes, from organisms as diverse as humans and E. coli. The desire for new sequence information has not been quenched by elucidation of these genomic sequences, however, as it has become apparent that individual variations in gene sequences play important roles in many physiological processes.

At the present time, most large scale sequencing efforts use the "chain termination", or Sanger method. In this method, polymerization of DNA is initiated at a specific site on a template by using a short oligonucleotide primer. The primer is extended with DNA polymerase in the presence of four deoxynucleotides, along with a low concentration of a chain terminating nucleotide, for example a dideoxynucleotide. Limited incorporation of the chain terminating nucleotide results in a set of overlapping DNA fragments that are all terminated at a position corresponding to the dideoxynucleotide. The fragments are then size-separated by electrophoresis, e.g. by PAGE, capillary electrophoresis, etc. Detection of the fragments can utilize radioactive or fluorescent tags, and variations of the method use dye-labeled primers, dye-labeled terminator nucleotides, and the like.

Other methods are known in the art that utilize size fractionation of fragments, for example the Maxam-Gilbert method, in which chemical reactions that selectively cleave DNA are used to generate the set of fragments. In addition, bulk techniques have been proposed that do not utilize sizing of fragments, including sequencing by hybridization, in which an array of short sequences of nucleotide probes is brought in contact with the target DNA sequence. A biochemical method determines the subset of probes that bind to the target sequence (the spectrum of the sequence), and a combinatorial method is used to reconstruct the DNA sequence from the spectrum.

There have been many proposals to develop new sequencing technologies based on single molecule measurements, for example by observing the interaction of particular proteins with DNA or by using ultra high-resolution scanned probe microscopy. Unlike conventional technology, their speed and read length would not be limited by the resolving power of electrophoretic separation. Single molecule sensitivity might permit direct sequencing of mRNA from rare cell populations or individual cells. A major obstacle has been the high data density of DNA. Scanned probe microscopes have not yet been able to demonstrate simultaneously the resolution and chemical specificity needed to resolve individual bases.

Braslavsky et al. (2003) PNAS 100:3960-3964 imaged sequence information from a single DNA template as its complementary strand was synthesized. DNA template oligonucleotides were hybridized to a fluorescently labeled primer and bound to a solid surface via streptavidin and biotin with a surface density low enough to resolve single molecules. The primed templates were detected through their fluorescent tags, their locations were recorded for future reference, and the tags were photobleached. A combination of evanescent wave microscopy and single-pair fluorescence resonance energy transfer was used to reduce background noise. Labeled nucleotide triphosphates and DNA polymerase enzyme were then washed in and out of the flow cell while the known locations of the DNA templates were monitored for the appearance of fluorescence. It was shown that DNA polymerase was active on surface-immobilized DNA templates and can incorporate nucleotides with high fidelity, although only a few nucleotide residues were actually sequenced. A disadvantage of this method is that it used information from many single molecule images to generate an ensemble measurement from which sequence information was extracted. Therefore information from many molecules was averaged together to obtain a single measurement.

An alternative method has been proposed (Akeson et al. (1999) Biophys J. 77(6):3227-33) in which single molecules of a polynucleotide are driven through a nanopore channel by an applied electric field. During translocation, nucleotides within the polynucleotide are reported to pass through the pore in sequential, single-file order because of the limiting diameter of the pore. It has been suggested that this passage could provide a means for discrimination between pyrimidine and purine segments. At this time however, nanopore sequencing is a theoretical method, with only limited lab bench results.

Methods of obtaining nucleotide sequences from small samples, down to single molecules, are of great interest for research, environmental and clinical purposes. The ability of such a method to provide information from a single molecule in the absence of averaging is desirable. The present invention addresses this issue.

Publications

Abbondanzieri et al. (2005) Nature 438:460-465 demonstrate direct observation of base pair stepping by RNA polymerase. Greenleaf et al. (2005) Phys. Rev. Lett. 95:208102 describe a passive all-optical force clamp for high-resolution laser trapping.

SUMMARY OF THE INVENTION

Methods are provided for determining the nucleotide sequence of a polynucleotide, where the polynucleotide may be present at a low to single molecule concentration. The methods of the invention record the motion of a nucleotide-selective, processive enzyme along a polynucleotide template, in a reaction mixture that alters the enzyme movement in a base specific manner. A system providing high spatial resolution is used to follow the motion of the processive enzyme, recording data for position of the enzyme versus time. The tracked motion may be translational or rotational. Characteristic signals derived from this motion are collected for one or a plurality of reactions and arranged in temporal order. The motion data are correlated with the base specific alteration of movement, and from these data the nucleotide sequence is derived.

In one embodiment of the invention, the processive enzyme is a polymerase, e.g. DNA dependent RNA polymerase, DNA dependent DNA polymerase, RNA dependent DNA polymerase (reverse transcriptase), and the like. Many such enzymes are known in the art. In other embodiments, the processive enzyme is other than a polymerase, e.g. helicase, exonuclease, etc. The processive enzyme may be coupled to an entity that provides for enhanced visualization of movement, e.g. bead, particle, etc.

In a related embodiment, the reaction mix comprises concentrations of nucleotides that cause a polymerase to alter its movement when catalyzing the addition of a specified base. The difference in enzyme motion during catalysis, (in some cases polymerization), of the specified nucleotide versus the non-specified nucleotides is detectable, and the trace of such a difference indicates the position of the complementary base in a polynucleotide template. In many embodiments at least four reactions are performed in a parallel or serial manner, where each reaction is movement altering for a different nucleotide. By appropriately combining and aligning data from the records of all four individual reactions, the temporal sequence of altered movement can determined, and thereby the sequence of bases is determined.

Examples of such reaction mixes include, without limitation, a mix that comprises a rate limiting concentration of one nucleotide, where the remaining three nucleotides are present at non-rate limiting concentrations, thereby causing the enzyme to pause for the catalysis of the rate-limiting nucleotide. Another reaction mix of interest comprises three rate limiting nucleotides, where the specified nucleotide is present at a non-rate limiting concentration. Another reaction mix of interest comprises a nucleotide analog that alters enzyme movement, present at a concentration sufficient to provide a detectable difference in movement. Such rate altering analogs may comprise a moiety that alters reaction kinetics, e.g. a boronate derivative, thiol ester derivative, etc.

The polynucleotide template is typically provided in a stretched configuration, such that the molecule is in a linear configuration. Such a configuration may be provided by various methods, including, without limitation, the optical trapping of one or both termini, the magnetic trapping of one or both termini, tethering of one terminus to a solid support and the other terminus to an optical trap, application of laminar fluid flow and the like.

In one embodiment, the DNA template is held in a passive optical force clamp, which operates passively by taking advantage of the anharmonic region of the trapping potential. In an optical trap, near the peak of the force-displacement curve is a region where the force is approximately constant for small displacements (i.e. zero stiffness). An object that is pulled into this region is effectively force-clamped. For example, the methods of the invention may use an instrument that comprises two trap beams, where one of the traps is less intense than the other. By attaching a polynucleotide template between two beads, the bead in the weaker trap can be pulled into the region of constant force (zero stiffness), while the bead in the stronger trap remains within the calibrated linear region. The template is thus held in a linear configuration during a processive enzyme reaction, allowing the movement of the processive enzyme to be tracked over time.

DETAILED DESCRIPTION OF THE EMBODIMENTS

Figure 1:
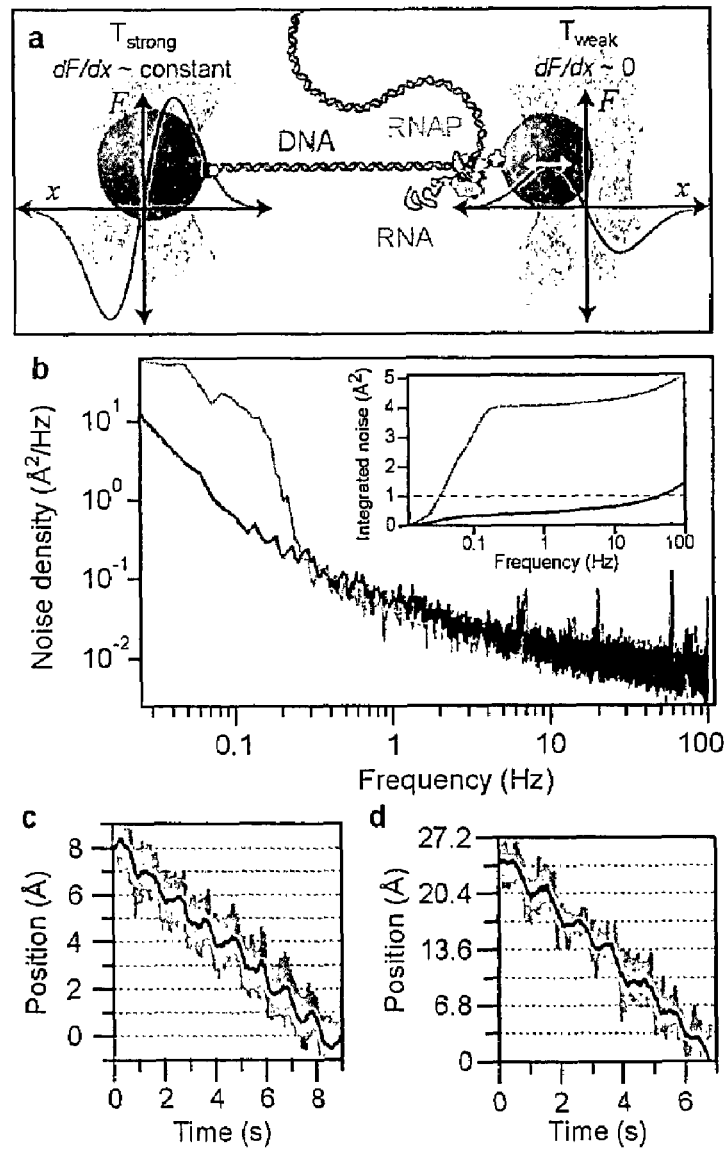
FIGS. 1a-d. Experimental set-up, passive force clamp, and sensitivity of the RNAP dumbbell assay. a, Cartoon of the dumbbell geometry with schematic force vs. position curves (dark red) shown for both trap beams (not drawn to scale). A single, transcriptionally-active molecule of RNAP (green) is attached to a bead (blue) held in trap $T_{weak}$ (pink, right) and tethered via the upstream DNA (dark blue) to a larger bead held in trap $T_{strong}$ (pink, left). The right bead is maintained at a position near the peak of the force-extension curve of $T_{weak}$, where trap stiffness vanishes (white arrow), creating a force clamp (trap stiffness k=dF/dx). During elongation, the DNA tether lengthens and the beads move apart. Due to the force clamp arrangement, only the right bead moves: displacement is measured for this bead. b, Power spectrum acquired for a stiffly trapped bead with external optics under air (red) or helium (blue). Inset: Integrated noise spectra for air (red) and helium (blue), showing a 10-fold reduction in power. c, Steps resolved for a stiffly trapped bead moved in 1 Å increments at 1 Hz. Data were median filtered with a 5 ms (pink) and 500 ms (black) window. d, Steps resolved for a bead:DNA:bead dumbbell held at 27 pN of tension, produced by moving $T_{strong}$ in 3.4 Å increments at 1 Hz and measuring the corresponding displacements in $T_{weak}$.

The nucleotide sequence of a polynucleotide is determined by tracking the motion of a nucleotide-selective, processive enzyme along a polynucleotide template, in a reaction mixture that alters the enzyme movement in a base specific manner. Characteristic signals derived from this motion are collected as traces of the position of the enzyme as a function of time. The enzyme movement traces are correlated with the reaction conditions, and from these characteristic signals, the nucleotide sequence is derived.

Polynucleotide template. As used herein, the term "polynucleotide" is given its common meaning, that is, a polymer of nucleotides, usually linked by phosphodiester bonds, which can hybridize with naturally occurring nucleic acids in a sequence specific manner analogous to that of two naturally occurring nucleic acids. Polynucleotides include naturally occurring adenine, guanine, cytosine, thymidine and uracil, and may also include 2'-position sugar modifications; propynyl additions, for example at the at the 5 position of pyrimidines; 5-position pyrimidine modifications, 7- or 8-position purine modifications, modifications at exocyclic amines, 5-methyl cytosine; 5 bromo-cytosine; alkynyl uridine and cytosine; inosine, substitution of 4-thiouridine, substitution of 5-bromo or 5-iodo-uracil; backbone modifications, including peptide nucleic acids (PNA), locked nucleic acids (LNA), etc., methylations, morpholino derivatives; phosphoroamidate derivatives; unusual base-pairing combinations such as the isobases isocytidine and isoguanidine and the like. Derivatives can also include 3' and 5' modifications such as capping.

The terms "ribonucleic acid" and "RNA" as used herein mean a polymer composed of ribonucleotides. The terms "deoxyribonucleic acid" and "DNA" as used herein mean a polymer composed of deoxyribonucleotides. The term "oligonucleotide" as used herein denotes single stranded nucleotide multimers of from about 10 to 100 nucleotides and up to 200 nucleotides in length. Polynucleotides include molecules up to the size of whole chromosomes, although for many purposes it is more convenient to utilize molecules of less than about 5,000 bases in length, and often less than about 1,000 bases in length, where fragmentation may be achieved using any convenient protocol, including but not limited to: mechanical protocols, e.g., sonication, shearing, etc., chemical protocols, e.g., enzyme digestion, etc.

Polynucleotides may be single, double, and in some instances, triple stranded. For the purposes of the invention, linear molecules will usually serve as templates, although circular molecules are readily converted to linear molecules. Methods of isolating polynucleotides from natural and synthetic sources are well-known in the art and need not be elaborated here.

The term "sample" as used herein relates to a material or mixture of materials, typically, although not necessarily, in fluid form, containing one or more components of interest. Polynucleotide sources of interest include clinical samples, e.g. cells from blood, biopsy, culture, hair, scrapings, etc., which may be of eukaryotic or prokaryotic origin. Samples of microbes include microbe communities and isolated strains. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; and the like. Samples are usually provided in a suspension or solution, and may contain as few as a single cell, usually at least about $10^2$, more usually at least about $10^3$, $10^4$, $10^5$ or more cells, and may contain from one, two, three, four, to tens, hundreds or more of different species. Polynucleotides may be prepared from a sample using any convenient protocol. In some embodiments, DNA or RNA is prepared by first obtaining a starting composition, for example a cell lysate or fraction thereof, where any convenient means for obtaining such a fraction may be employed and numerous protocols for doing so are well known in the art, e.g. detergent lysis, French press, freeze thaw, etc.

Following provision of a polynucleotide, templates may be prepared for sequencing. It should be emphasized that the nature of the present invention allows for sequencing of very small sample sizes, and in one embodiment of the invention, the need for cloning, amplification, etc. of a template is bypassed, and a sample is directly processed for sequencing.

In other embodiments it will be desirable to sequence a specific region of a larger molecule. Such selectivity can be accomplished by cloning into a vector of interest, specific amplification of the region of interest, or the like. Alternatively, hybridization primers may be utilized to select a sequence of interest for sequencing. In such methods, a primer of from about 12 to about 100 nucleotides in length that selectively hybridizes to at least one region of a sequence of interest is hybridized to the target polynucleotide, which may be denatured for hybridization. One or more primers may be used. The primer is optionally coupled to a entity for trapping, e.g. magnetic trapping, optical trapping, coupling to a solid substrate, etc., and such a entity is optionally used for selection of the targeted polynucleotide prior to sequencing. For example, a magnetic or paramagnetic particle may provide a means of selecting a desired polynucleotide, and may then be utilized in trapping. Alternatively, a biotinylated primer may be used for affinity selection of the desired polynucleotide, and subsequently find use in coupling to a substrate for trapping. Depending on the processive enzyme that is selected, the primer may also serve to initiate polymerization, e.g. as a primer for polymerization, to provide an initiation site for transcription, and the like.

In some embodiments of the invention, the template is stretched between two traps. In such embodiments, typically one or both termini of the template are coupled to a solid support. The support can have a variety of configurations, e.g., a sheet, bead, or other structure, often a bead. Preferred supports can be trapped or otherwise immobilized, e.g. optically, physically, magnetically, etc. In some instances the support may comprise an array, which includes any one-dimensional, two-dimensional or substantially two-dimensional (as well as a three-dimensional) arrangement of addressable regions bearing nucleic acids, particularly oligonucleotides or synthetic mimetics thereof (i.e., the oligonucleotides defined above), and the like. The polynucleotides may be adsorbed, physisorbed, chemisorbed, or covalently attached to the support at any point or points along the nucleic acid chain.

Where the template is to be magnetically trapped, the support may be a magnetic or paramagnetic particle. Supports for optical trapping are typically a high dielectric material that does not absorb light, e.g. polystyrene, silica, etc. Supports for physical trapping include polyacrylamide, nylon, nitrocellulose, polypropylene, polyester, glass, fused silica, quartz, plastics, e.g. polytetrafluoroethylene, polypropylene, polystyrene, polycarbonate, and blends thereof, and the like; metals, e.g. gold, platinum, silver, and the like; etc.

The template may be directly or indirectly coupled to the support. For direct coupling, the linkage may be a homo- or heterobifunctional linker having a group at one end capable of forming a stable linkage to the template, and a group at the opposite end capable of forming a stable linkage to support. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP) or 4-(N- maleimidomethyl)-cyclohexane-1-carboxylic acid N-hydroxysuccinimide ester (SMCC).

Indirect coupling may utilize a specific binding member, which as used herein refers to a member of a specific binding pair, i.e. two molecules, usually two different molecules, where one of the molecules through chemical or physical means specifically binds to the other molecule. Specific binding pairs of interest include antibodies and antigens; carbohydrates and lectins; complementary nucleotide sequences (including nucleic acid sequences used as probes and capture agents in DNA hybridization assays); peptide ligands and receptor; effector and receptor molecules; hormones and hormone binding protein; enzyme cofactors and enzymes; enzyme inhibitors and enzymes; and the like. Moieties such digoxin, digoxigenin, FITC, dinitrophenyl, nitrophenyl, avidin, streptavidin, biotin, etc. may be used as haptens for antibody binding, or in some cases, e.g. biotin, may be used with their specific binding partner. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present. Methods for conjugation of such binding partners to a polynucleotide are known in the art, and kits for such conjugations are commercially available. Empirical binding assays may be performed to determine the optimal ratio of hapten to allergen for the subject analysis.

Processive enzyme. A processive enzyme catalyzes multiple rounds of a reaction, e.g. elongation, digestion, unwinding, etc. on a polymer, while the polymer stays bound to the enzyme. A distributive enzyme, in contrast, releases its polymeric substrate between successive catalytic steps. Enzymes that catalyze reactions relating to polynucleotides are particularly known for their potential to be processive. For use in the methods of the invention, an enzyme will be processive, i.e. on average will stay bound to the template, for at least about 25 nt.; at least about 50 nt; at least about 100 nt, usually at least about 500 nt, and may be processive for at least about 1000 nt or more.

In some embodiments of the invention, the processive enzyme is a polymerase. Polymerases include DNA polymerases, which may be DNA dependent, e.g. pol I, pol III, etc.; or RNA dependent, e.g. reverse transcriptase, etc.; and RNA polymerases, which may be DNA dependent, e.g. RNA polymerase, the eukaryotic RNA polymerases PolI, PolI and PolIll; or RNA dependent, e.g. rdp1, RDRP, etc. The selection of polymerase may be based on the desired template, i.e. RNA, DNA, etc.; requirement for initiation primer or specific initiation site; length of sequence to be determined; presence of proof-reading functions, and the like.

A review of eukaryotic DNA polymerases may be found in Hübscher et al. (2002) Ann. Rev. Biochem. 71:133-163 (herein specifically incorporated by reference). Polymerases include enzymes belonging to any of the following enzyme classifications, as listed in the protein database: EC 2.7.7.6 DNA-directed RNA polymerase. [71 PDB entries]; EC 2.7.7.7 DNA-directed DNA polymerase. [288 PDB entries]; EC 2.7.7.8 Polyribonucleotide nucleotidyltransferase. [2 PDB entries]; EC 2.7.7.31 DNA nucleotidylexotransferase. [4 PDB entries]; EC 2.7.7.48 RNA-directed RNA polymerase. [75 PDB entries]; and EC 2.7.7.49 RNA-directed DNA polymerase. [76 PDB entries], which public information is herein specifically incorporated by reference.

Polymerases vary in their processivity. For example, E. coli polymerase I is reported to be processive only for short sequences, while DNA polymerase III holoenzyme is highly processive, and catalyzes the formation of many thousands of phosphodiester bonds before releasing its template. Other enzymes reported to be highly processive include, without limitation, Bal31 nuclease; pfx DNA polymerase, taq polymerase, T7 DNA polymerase, which may be provided with or without 3' to 5' exonuclease and 5' to 3' exonuclease activity; phi29 DNA polymerase; RNA polymerases including E. coli, SP6, T7, T3, etc.

Other nucleic acid enzymes are processive, including, for example, DNA helicases, RNA helicases, exonucleases, etc. For example, E. coli RecBCD is a processive enzyme with both helicase and nuclease activities. Processive exonucleases include, without limitation, snake venom phosphodiesterase, which is processive from the 3'-end of DNA and RNA; spleen phosphodiesterase, which is processive from the 5'-end of DNA and RNA; lambda exonuclease; XPF/Mus81 family of structure-specific nucleases, and the like.

The processive enzyme may be coupled to an entity for trapping or for enhancing detection in some embodiments of the invention. As described above, various moieties, including beads, are known in the art and may be coupled to the enzyme by direct or indirect methods.

Initiation. Certain polymerases may require a particular structure for initiation of the reaction. For example, certain RNA polymerases may require general transcription factors and a promoter sequence (TATA box) for initiation of transcription. Other polymerases, e.g. Pol I, may require a primer to be present to initiate polymerization. Depending on the needs of the enzyme that is selected, a primer may be hybridized to the template to initiate the reaction. The use of such primers is well-known in the art. Primers may be at least about 8 nucleotides in length, usually at least about 12 nt in length, more usually at least about 16 nt in length, at least about 20 nt in length, at least about 25 nt in length, and usually are not more than about 200 nt in length, more usually not more than about 100 nt, or 50 nt in length. Annealing of primers to templates may be accomplished with partial or complete denaturation, where denaturation may be thermal, chemical, etc.

In reactions that require a specific initiation site, a primer comprising the initiation sequence may be ligated to the target polynucleotide using conventional methods. Alternatively a hybridization strategy, amplification methods, and the like as known in the art may be used to introduce an initiation sequence.

Reaction mixture. The processive movement of an enzyme is typically manifested in an in vitro reaction comprising a polynucleotide template, nucleotides or deoxynucleotides, and such buffers and other reagents as are necessary. Such synthetic reaction systems are well known in the art, and have been described in the literature.

Reactions for the methods of the invention also provide conditions that alter the enzyme movement in a base specific manner, usually by retarding or increasing the time the enzyme takes to react with one of the nucleotides, i.e. G, A, T/U and C. By altering the movement associated with one of the bases, a trace of the enzyme movement along the length of the polynucleotide will display characteristic changes in motion at each occurrence of the selected base, and this change in motion, when recorded, provides an indication of where on the template the selected base is found. It will be understood by one of skill in the art in polymerization reactions that the base being added is complementary to the template strand.

In some embodiments, methods are used to selectively retard the enzyme at a specific base. In one embodiment, the concentration of one nucleotide is selected to be rate limiting in a polymerization reaction. The rate limiting nucleotide is present at a concentration that allows polymerization to proceed for the desired length of template, but that causes a "hesitation", or detectably longer period of time for a nucleotide to be added to the chain. The rate limiting concentration for a particular enzyme may be empirically derived, or based on the known substrate requirements for the enzyme. The non-rate-limiting nucleotides will be provided at optimal concentrations for the enzyme, or higher. Alternatively, customized reaction mixtures may be designed to have equal reaction times for the non-rate limiting nucleotides, for example as described in Example 1.

Working concentrations may range from at least around about 50 µM, around about 500 µM, around about 1 mM, and typically do not benefit from concentrations higher than around about 10 mM. The rate limiting nucleotide will be present at a concentration that is usually not more than about 25% of the enzyme's optimal concentration, not more than about 10% of the enzyme's optimal concentration, not more than about 1% of the enzyme's optimal concentration, to not more than about 0.1% of the enzyme's optimal concentration or less. In some examples, the rate limiting nucleotide will be present at a concentration of not more than about 100 µM, about 25 µM, about 5 µM, about 2.5 µM or less.

Alternatively, the rate altering nucleotide may comprise a nucleotide analog that is more slowly or more quickly reacted by the processive enzyme for reasons of steric hindrance, hybridization kinetics, rate of phosphodiester bond formation, etc. The rate limiting nucleotide analog allows polymerization to proceed for the desired length of template, but causes a detectably different period of time for a nucleotide to be added to the chain, and therefore chain termination nucleotides are usually not used in the methods of the invention. The rate altering concentration for a particular enzyme may be empirically derived, or based on the known substrate requirements for the enzyme. Polymerases vary in their substrate utilization, and thus the specific choice of analog may be based on empirical studies or known enzyme requirements.

Known nucleotide analogs include dUTP, biotinylated dNTPs and NTPs, 7-deaza-dGTP, digoxigenin-dNTPs and NTPs, bromo-dNTPs and NTPs, ITP, fluoresceinated dNTPs and NTPs; and the like. It has been reported that analogs with modifications at the base moiety are less likely to affect the rate of chain elongation, whereas those modified at the sugar moiety are more likely to inhibit the rate of chain elongation (see Frank et al. (1985) Adv Enzyme Regul. 24:377-84). Comparative kinetic analyses of a variety of polymerases have revealed elements of nucleotide discrimination, and have shown nucleotide analogs that affect, inter alia, affinity of NTP binding, rate of phosphoryl transfer, rate of phosphodiester bond formation, etc. (see Gardner et al. (2004) J. Biol. Chem. 279:11834-11842). For example, 2'-deoxynucleoside 5'-alpha-borano triphosphates and thiophosphates have been reported to have an efficiency of from about 15% to about 30% of native dNTPs. Morpholino phosphates are also useful substrates and have been show to have altered efficiency for certain polymerases.

The reaction mix may also be designed to enhance the efficiency of a selected nucleotide. In one such embodiment, three nucleotides are absent while the fourth is present at a non-rate limiting concentration. By rapidly cycling the single present nucleotide in the reaction mixture through all four possible species and correlating enzyme motion with nucleotide species present during the motion, sequence information can be built up from a single molecule.

Alternatively, certain analogs have an enhanced efficiency for certain enzymes relative to the native nucleotides, and this will provide for a shortened time for enzyme motion during catalysis of the analog.

Trapping. In one embodiment of the invention, an optical trap is used to hold the DNA template in a stretched configuration. Optical traps use a laser beam brought into tight focus to change the gradient forces surrounding dielectric particles, where the radiation pressure traps particles. Optical trapping is described, e.g. in U.S. Pat. No. 4,893,886, as a single-beam gradient force trap. This force trap consists of a strongly focused light beam which has a near Gaussian transverse intensity profile. The stabilizing effect on the trapped particle arises due to the combination of the radiation pressure scattering and gradient force components, which combine to give a locus of stable equilibrium near the focus of the laser beam. Thus, stabilizing the trapped particle occurs by strongly focusing the light. The majority of currently produced optical tweezer systems create a single or a few tweezers, moving a singular or a few particles at a time. Dual beams of light have been used as optical tweezers to manipulate microscopic objects and cells. Both single and dual-beam traps were used to levitate a microsphere from the bottom of a sample chamber (Ashkin (1991) ASGSB Bull. 4(2):133-46).

In one embodiment, the DNA template is held in a passive optical force clamp, which operates passively by taking advantage of the anharmonic region of the trapping potential. In an optical trap, near the peak of the force-displacement curve is a region where the force is approximately constant for small displacements (i.e. zero stiffness). An object that is pulled into this region is effectively force-clamped. For example, the methods of the invention may use an instrument that comprises two trap beams, where one of the traps is less intense than the other. By attaching a polynucleotide template between two beads, the bead in the weaker trap can be pulled into the region of constant force (zero stiffness), while the bead in the stronger trap remains within the calibrated linear region. The template is thus held in a linear configuration during a processive enzyme reaction, allowing the movement of the processive enzyme to be tracked over time.

In order to stretch the template, two separate forces may be exerted on the template-enzyme complex, where a first trapping force may be exerted on the template itself, and a second trapping force exerted on the template molecule, or more usually, on the moving enzyme. Various combinations of forces may be used, physical immobilization, magnetic trapping, optical trapping, laminar fluid flow, etc. In some embodiments, the first trapping force is selected from physical, magnetic, optical, etc. trapping forces, and the second trapping force is a passive optical trap, as described herein, which provides a stable force on a moving object. In many instances the template and the enzyme are separately coupled to moieties that allow for, or enhance trapping, e.g. a solid substrate that may be a bead, planar surface, etc.

Alternative configurations allow for detection of rotation. By coupling the processive enzyme that follows the helical pitch of the polynucleotide template to an entity that that can be rotationally tracked (e.g. through fluorescence polarization, asymmetrically fluorescent beads, birefringence etc.), an entire field of particles similarly coupled on a microscope slide can be tracked rotationally, and thus sequenced in parallel. Various methods may be used to extend the polynucleotide template in order to visualize the rotation, including the methods described above for tracking. In a miniaturized system, the scattering force of an unfocused laser may be used to exert force on the enzyme-coupled entity in order to extend the DNA tether. Alternatively, magnetic beads may be coupled to the processive enzyme, and used to apply force to the tethers. In an alternative configuration, an array of nanofabricated pores is used to rotationally sequence DNA. In a solid substrate, a large array of small holes between 2 and 500 nm in diameter may be created by electron-beam lithography, ion etching etc. Then one may attach enzymes initiated on the polynucleotide template to a small rotationally detectable non-magnetic bead between 1000 and 5 nm in diameter (as described above) which is larger in diameter than the holes. Electrophoresis or fluid flow may be used to thread the template through the pore, leaving the beads sitting above the pore free to rotate, like a ball and socket joint. Then magnetic beads are attached to the distal end of the template, rotationally constraining this end of the template and applying force to elongate the template. As the enzyme tracks the helical pitch of DNA, the rotationally detectable bead attached to the enzyme (the only component of the dumbbell which is not rotationally constrained) will be forced to rotate as well, giving a readout of the progress of the enzyme in angle-space. By either flowing a single limiting nucleotide concentration, or sequentially flowing single species of nucleotide (as discussed previously), an entire microscope field-of-view is sequenced via the detection of fluorescence rotation or simple bright-field imaging.

Sequencing Methods

The methods of the invention require exceedingly small amounts of polynucleotide template, and can be performed with as few as a single template, usually as few as 4 templates, and may be performed in series or parallel experiments to reduce experimental variation, i.e. performed in duplicate, in triplicate, etc. The methods thus provide an opportunity to obtain sequence information from sources where the absolute number of template molecules is low, e.g. various environmental, criminal, clinical samples, etc. as described above. The low template requirement also allows the methods to be performed in the absence of amplification of the target sequence, where amplification refers to any method of replicating a polynucleotide sequence, either in vitro, e.g. PCR, etc. or in vivo, e.g. cloning by recombinant methods.

The polynucleotide template is arranged in a "tracking configuration", which configuration is a physical state that allows tracking the motion of a processive enzyme moving along the template. In one embodiment of the invention, the tracking configuration is a stretched configuration. Various physical forces may be used to achieve the tracking configuration, e.g. immobilization on a solid substrate, trapping, etc. The tracking configuration may be achieved before or after contact of the template with a processive enzyme, but will usually be achieved prior to measurements of motion. In one embodiment, the tracking configuration utilizes a dumbbell configuration, where the template is stretched between two trapped particles.

A processive enzyme is brought into contact with the template in a reaction mixture that is sufficient for catalysis of the reaction associated with the enzyme, but in which the enzyme movement is altered in a base specific manner, usually by retarding or increasing the time the enzyme takes to react with one of the 4 nucleotides, i.e. G, A, T/U and C. Included in such conditions are any primers, initiation factors, etc. that are required for activity of the processive enzyme.

In some embodiments of the invention, the reaction for each nucleotide is performed in parallel on different templates, thus requiring 4 separate reactions. In another embodiment of the invention, the reaction for each nucleotide is performed serially on a single template, thus requiring only a single polynucleotide molecule for sequence determination. In such embodiments, the reaction mixture may be washed out or otherwise altered between reactions. For example, a reaction may be initially run with 3 rate-limiting nucleotides and one non-rate limiting, and with each successive enzyme run, the concentration of one nucleotide is increased to a non-rate limiting level. Alternatively the reaction mixture may comprise non-rate limiting concentrations of 3 nucleotides, after which it is washed out or diluted so as to alter which nucleotide is rate-limiting.

Enzymes suitable for serial methods include, without limitation, RNA polymerase to transcribe multiple mRNA molecules from a single template, where transcription is re-initiated with each rate altering reaction mix; polymerases having sufficient exonuclease activity to "chew back" a newly synthesized strand, and the like.

The movement of the enzyme is monitored by methods known in the art. For example, in the examples provided herein, a detection laser is used to detect the position of the enzyme-coupled entity. This laser (for example 30 mW, 830 nm diode laser from Point Source, UK) is deflected by the motions of the enzyme-coupled entity, and these deflections are monitored using back focal plane detection on a position sensitive detector (PSD, Pacific Silicon Sensors). The PSD gives a readout of the position of the detection laser, which is a function of where the entity is in the optical trap. Another common imaging method used in optical trapping assays to detect position of beads is optical-trapping interferometry, which is rather like differential interference contrast microscopy. Motion detection is also accomplished using fluorescent particles (such as quantum dots, or simple fluorescent beads) or even single fluorophores. Alternatively, atomic force microscopy is used to detect the position of the enzyme by attaching a cantilever to the enzyme and measuring deflections of this cantilever.

To determine the sequence of the template, the traces of the enzyme motion are recorded and aligned, e.g. with a known initial sequence, etc., and the movements associated with each movement altering nucleotide are compiled. Alignments of the recorded motions can be accomplished through a number of methods (for examples, see Herbert et al. "Sequence-resolved detection of pausing by single RNA polymerase molecules", Cell, 125:1083-1094 and Greenleaf and Block "Single-molecule, motion-based DNA sequencing using RNA polymerase", Science, 313:801). Generally these alignments require autocorrelation of the position dwell-time histogram with an expected position histogram in a known "primer" region in order to obtain initial spatial alignment These aligned raw signals may be analyzed by a signal processing software. The steps of signal processing may include downsampling of the data to 1 Hz if necessary, primer data removal, baseline adjustment, noise filtering, multicomponent transformation, mobility shift correction, signal normalization, etc. (see, e.g., M. C. Giddings, et al., "A Software System For Data Analysis In Automated DNA Sequencing", Genome Research, vol. 8, pp. 644-665 (1998)). To increase signal-to-noise, multiple records of different enzyme motions under identical conditions can be averaged together to generate an ensemble-average motion prior to further processing.

Processing the raw data produces analyzed traces with defined peaks. The analyzed data in the form of traces may then be processed using a base calling program. The base calling program infers a sequence of bases in the polynucleotide template. This sequence of bases is also referred to as a read. Not all of the called bases are used in subsequent processing. The statistically averaged error produced by any base calling program is usually low, i.e., below 1%, for bases located near middle of a read and may increase toward the end of a read. To characterize a reliable, or high quality part of a read, a threshold of 1% base calling error is commonly accepted. That is, only that part of the read having an average base calling error of 1% or less will be subsequently used. Alternatively, this may be characterized in terms of the quality values assigned to bases, where the quality is the measure of reliability of the base call. According to a commonly used definition of quality values, a quality value of 20 or higher corresponds to a probability of error of 1% or less. In practice, when sequencing, the correct sequence is not known in advance, so reliable predictions of quality values for newly sequenced fragments based on previous training or calibration on a data set with a known correct sequence are desirable.

Software packages suitable for calling bases are known in the art and commercially available, e.g. ABI Base Caller is a part of DNA Sequencing Analysis software produced by Applied Biosystems of Foster City, Calif. Phred is a base calling software program that achieves a lower error rate than the ABI software, and is especially effective at the end of a read. Phred can be adapted to the methods of the invention by utilizing enzyme movement traces as input data. For information on the software, see B. Ewing, et al., "Base Calling of Automated Sequencer Traces Using Phred. I. Accuracy Assessment", Genome Research, vol. 8(3), pp. 175-185 (1998); B. Ewing and P. Green, "Base-Calling Of Automated Sequencer Traces Using Phred. II. Error Probabilities", Genome Research, vol. 8(3), pp. 186-194 (1998). Further analysis may also be performed according to the requirements of the specific application of the methods. For example, given a detailed kinetic model of the enzyme used for sequencing, certain bases in certain sequence contexts might be expected to have a next-nucleotide addition rate different from other positions, and therefore peaks which are larger or smaller than the average. A base-calling algorithm could take advantage of this a priori information about the kinetics of the enzyme itself to increase the accuracy of base calls, by comparing the expected size of the peaks generated to the actual peaks, and using the agreement as a base assignment metric. For example, average pause lifetimes for different positions on the DNA template are known to vary by more than an order of magnitude for RNA polymerase (see Abbondanzieri et al. (2005) Nature 438, 460). If the contribution of the identity of the different bases underfoot of the enzyme is known, then the height of the dwell time can also give information about the most likely sequence underfoot of the enzyme, which can be extracted using a maximum likelihood method, a hidden-Markov model, etc. The characterization of the next-nucleotide addition rates for different sequences underfoot of the enzyme can significantly increase the amount of information obtained from each individual dwell event.

The resulting polynucleotide sequence information may be output electronically, saved to files, etc.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following example is put forth so as to provide those of ordinary skill in the art with a complete disclosure and description of how to make and use the subject invention, and is not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Experimental

EXAMPLE 1

Direct Observation of Base-Pair Stepping by RNA Polymerase

During transcription, *E. coli* RNAP translocates along DNA while following its helical pitch, adding ribonucleoside triphosphates (NTPs) successively to the growing RNA. The basic reaction cycle consists of binding the appropriate NTP, incorporation of the associated nucleoside monophosphate into the RNA, and release of pyrophosphate. In addition to following the main reaction pathway, RNAP can reversibly enter any of several off-pathway paused states. For example, RNAP may backtrack by several bases along DNA, displacing the RNA 3'-end from the catalytic centre and temporarily inactivating the enzyme. Paused states complicate the interpretation of biochemical studies of RNAP elongation because these kinetic measurements convolve on- and off-pathway events into overall rates. The resolution of individual enzymatic turnovers would be especially helpful in unraveling the behavior of complex reaction cycles for enzymes such as RNAP.

Construction of an ultra-stable optical trap. Because the distance spanned by a base pair is so small, it was necessary to construct a stable optical trapping system capable of ångström-level resolution. Sources of noise that hamper optical measurements include drift of the microscope stage (or other nominally stationary components), pointing fluctuations leading to relative motions of the laser beams used for trapping and position detection, and brownian motions of the trapped bead itself. To minimize the noise associated with stage motions, we employed a dual-trap "dumbbell" arrangement, as described by Shaevitz et al. (2003) Nature 426:684-7. In this geometry (FIG. 1a), all components of the assay are optically levitated above the coverglass surface and thereby decoupled from stage drift. A stalled transcription complex containing a biotin-tag on the C-terminus of the β' subunit was specifically attached via an avidin linkage to the surface of a 600-nm diameter polystyrene bead. Depending on the desired direction of applied load, either the transcriptionally upstream or downstream end of the DNA was then bound via a digoxygenin:antibody linkage to a 700-nm diameter bead, forming a bead:DNA:RNAP:bead "dumbbell". Dumbbells were suspended ~1 μm above the microscope coverglass by two independently steered traps, $T_{weak}$ and $T_{strong}$.

To isolate the detection and trapping beams from the effects of random air currents, which introduce density fluctuations that perturb the positional stability of laser beams, we enclosed all optical elements external to the microscope in a sealed box filled with helium gas at atmospheric pressure. Because the refractive index of helium is closer to unity than that of air ($n_{He}$=1.000036 vs. $n_{air}$=1.000293), density fluctuations introduce smaller deflections. Using helium, we realized a 10-fold reduction in the noise spectral density at 0.1 Hz for a stiffly trapped, 700 nm diameter bead (k=1.9 pN/nm), and the integrated system noise power remained below ~1 Å over the bandwidth of interest (FIG. 1b). To illustrate the resolution achieved, we moved a trapped bead in increments of 1 Å at 1 s intervals by displacing $T_{strong}$ with an acousto-optic deflector (AOD). Steps were clearly resolved, with signal-to-noise ratio of ~1 over a 100 Hz bandwidth (FIG. 1c).

Finally, we implemented a recently-developed method to maintain constant force on trapped beads using an all-optical arrangement, without the need for computer feedback. Such a passive force clamp eliminates artifacts associated with feedback loops and provides exceedingly high bandwidth. To create this clamp, the bead in $T_{weak}$ was maintained in a ~50 nm region near the maximum of the force-extension curve, where the force is independent of bead position. Force clamps eliminate the need for elastic corrections due to either the compliance of $T_{strong}$ or the stretching of the DNA along with its associated linkages, so that all molecular displacements are registered in the motion of the bead in $T_{weak}$. To demonstrate the resolution achieved in our setup, a dumbbell consisting of beads connected by a DNA tether (but no RNAP enzyme) was stepped in increments of 3.4 Å at 1 Hz (FIG. 1d).

RNA polymerase takes single base-pair steps. To resolve individual translocation events, we required that RNAP transcribe slowly enough to time-average to the ångström level over positional uncertainties caused by brownian motions, but quickly enough so that long-term drift did not obscure motion. Because RNAP has different average rates of addition for the four species of nucleotide, we determined by gel analysis the concentration ratios at which each species becomes equally rate limiting for elongation on our template. Unless otherwise noted, our experiments were conducted at $[NTP]_{eq}$=10 μM GTP, 10 μM UTP, 5 μM ATP, and 2.5 μM CTP, concentrations which produce a mean elongation rate of ~1 bp/s under our conditions.

Figure 5:
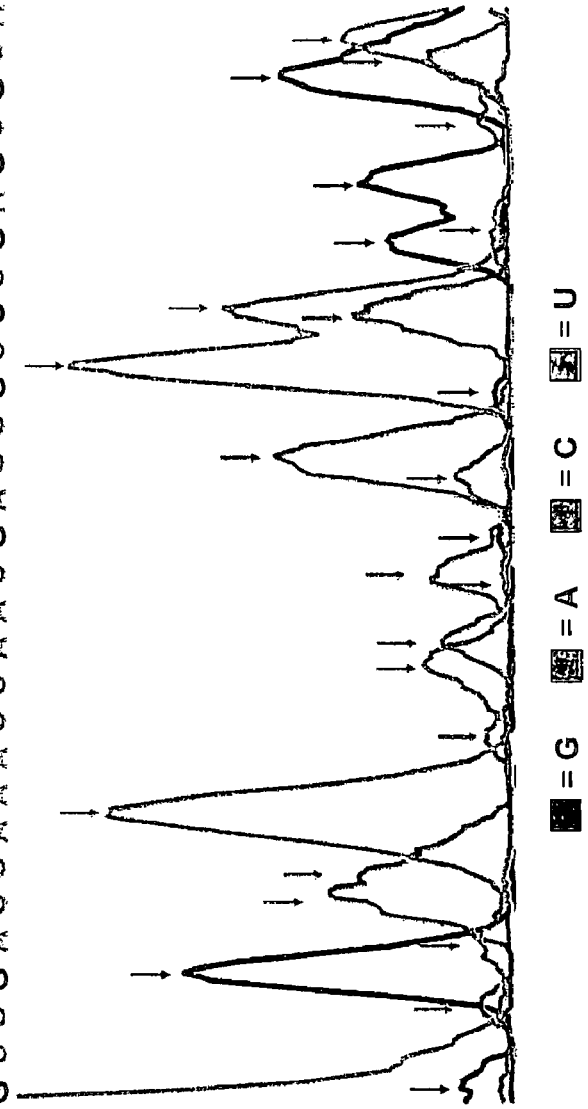
FIG. 5 shows processed position histograms from the records in FIG. 3. These histograms have been slightly attenuated and normalized. Bases can be detected by first calling peaks which occur within a base-pair window, then resolving peak conflicts by assigning peaks to the nearest unassigned base-pair window, and finally calling the highest traces within a 0.34 nm basepair window. (SEQ ID NO: 2)

In single-molecule records of transcription by RNAP selected for their low noise and drift, we observed clear, stepwise advancements. FIG. 5a shows six representative traces obtained under 18 pN of assisting load. Although dwells at some expected positions (FIG. 2a, dotted lines) were missed or skipped, steps were uniform in size, corresponding to nearly integral multiples of a common spacing. To estimate this fundamental spacing, we performed a periodogram analysis. The position histograms for 37 segments derived from transcription records for 28 individual RNAP molecules were computed and the autocorrelation function calculated for each of these. These autocorrelations were combined into a global average which displays a series of peaks near multiples of the mean spacing (FIG. 2b), with the first and strongest peak at 3.4±0.8 Å. The power spectral density of this function measures the corresponding spatial frequencies and displays a prominent peak at the inverse of 3.7±0.6 Å (FIG. 5c). This distance is consistent with the crystallographic spacing between neighboring base pairs in B-DNA (3.4±0.5 Å). Although the foregoing analysis was performed on selected traces, a fully automated procedure was also conducted on a continuous, ~300 bp record of elongation, and returned a similar spacing of 3.7±1.5 Å.

The dramatic improvement in resolution obtained in this optical trapping study has led to the first direct measurements of base-pair stepping by an individual enzyme and supplied insights into the molecular mechanism of transcription by RNAP. The techniques presented here are broadly applicable. In particular, the approach is useful in utilizing the behavior of a nucleic acid-based enzyme directly to the underlying DNA sequence to which it is bound, facilitating studies of sequence-dependent effects in replication, transcription, and translation, and in single-molecule DNA sequencing. The ability to detect motions at the ångström scale in single enzymes opens new avenues for the study of biomolecules.

Methods

Optical trapping. Salient modifications to our apparatus include the construction of a sealed optics enclosure where helium gas at atmospheric pressure replaces ambient air, and the implementation of a passive, all-optical force clamp. The force-clamp was calibrated by measuring the relaxation rate of a 700 nm polystyrene bead (Bangs Labs) after release from a point ~300 nm from the trap centre. In this low-Reynolds-number regime, the velocity is proportional to the force acting on the bead: using this relationship, we found that force remained constant within 5% over a 50 nm-wide clamp region located ~220 nm from the trap centre. During single-molecule transcription experiments, the bead held in $T_{weak}$ was maintained in this zero-stiffness zone by occasionally moving $T_{strong}$ by 20 nm whenever the 600 nm bead in $T_{weak}$ approached the outer limit of the clamp region.

For collection of force-velocity data (only), we employed an active, AOD-based force clamp which allowed us to alter rapidly the load on an individual enzyme during a single run, and thereby to cover the entire range of forces. Each RNAP molecule included for analysis was subjected to a cycle of hindering (−5, −10, −14, −18 pN) or assisting (5, 10, 14, 18, 22, 29 pN) loads until it either terminated or stalled. By generating data for each molecule over a range of forces, we minimized variations due to intrinsic velocity heterogeneity.

Data analysis. Unless noted, bead displacement data were filtered with a 1 kHz, 4-pole Bessel filter, digitally acquired at 2 kHz, and median-filtered at 50 ms or 750 ms. To determine RNAP step size, we selected 37 segments of transcription through 51 Å-wide windows from 28 molecules at 18 pN or 27 pN of assisting load, then generated position histograms for each of these traces using a bin size of 0.1 Å. Histograms were autocorrelated, normalized by the number of data points, and averaged to form a global autocorrelation function. The power spectrum derived from this autocorrelation function was smoothed with a 5-point binomial filter.

EXAMPLE 2

A Passive all-optical Force Clamp for High Precision Laser Trapping

Here, we introduce a simple approach that operates passively by taking advantage of the anharmonic region of the trapping potential. As displacement from the center of the trap increases, force initially increases linearly (i.e. constant positive stiffness), then rolls over upon reaching a maximum and decreases to zero in the region outside the trap. Near the peak of the force-displacement (F-x) curve, there exists a region where the force is approximately constant for small displacements (i.e. zero stiffness). An object that is pulled into this region is effectively force-clamped, in the sense that the optical force acting on it does not vary with displacement. The load applied by such a force clamp can be set to the desired value simply by adjusting the intensity of the laser light.

Our instrument uses two 1064 nm trap beams with orthogonal linear polarizations produced by a single Nd:YVO$_4$ laser, whose positions and intensities are controlled independently by acousto-optic deflectors (AODs). Two independently positioned 633 nm detector beams with orthogonal polarizations produced by a single HeNe laser measure the positions of objects in the two traps, using position-sensitive detectors that monitor the light scattered by the trapped objects in the back focal plane. The force clamp is implemented as follows: First, one of the two traps (T1) is made roughly threefold less intense than the other (T2). Then, by attaching a molecule of double-stranded DNA (dsDNA) between two beads, the bead in the weaker trap (T1) can be pulled out from the center of T1 into the region of constant force (zero stiffness), while the bead in the stronger trap (T2) remains within the calibrated linear region. Displacements at constant force can thus be followed in T1 while force is recorded simultaneously in T2.

We measured the F-x curve of T1 using a 550 nm tether of dsDNA, attached at one end by a biotin:avidin linkage to a 600 nm diameter polystyrene bead and at the opposite end by a digoxigenin:anti-digoxigenin linkage to a 700 nm diameter polystyrene bead. The displacement of the bead in T1 versus the force measured in T2 is shown in FIG. 1B. For small displacements, the stiffness is constant, and the nearly linear F-x curve agrees very well with an independent calibration of T1 based on the Stokes drag force for an untethered bead of the same size. For displacements ~240 nm from T1, there is a zone >50 nm wide where force remains constant to within <5%: we use this zero-stiffness region for the force clamp. For positive displacements beyond this zone, the stiffness becomes negative as the force falls toward zero. The measured F-x relation fits well to the derivative of a Gaussian, the shape expected for a Gaussian beam in the paraxial, small-bead approximation, and is in qualitative agreement with previous measurements of the nonlinear portion of an optical trap.

We note that the measured F-x relationship exhibits significant nonlinearity in the restoring force even for relatively modest displacements from the trap center. From the fit to the F-x curve, we find that the stiffness at x=50 nm is ~8% less than the stiffness at the center of the trap, while at x=100 nm it is ~25% less. This deviation represents an important yet generally neglected source of systematic error when using optical traps to make quantitative measurements of force, especially when operating at typical displacements of 50-100 nm or more from the trap center.

In addition to the bandwidth limit arising from the relaxation time for the bead/handle attachments, a second practical limitation of the passive force clamp technique described here is the size of the zero-stiffness region used for the force clamp (~50 nm). While sufficiently large to study the folding/unfolding of small molecules, this region may be too small for the study of processive motors that can move hundreds of nm. This difficulty can be overcome fairly simply, however, by using traditional active feedback methods to keep the bead within the zero-stiffness region of the trap as the molecule moves. A constant force is maintained during the feedback-induced motion of the trap as long as the bead remains in the zero-stiffness region.

In summary, we have shown that by operating an optical trap in the zero-stiffness region of the trapping potential, we can exert a nearly constant force over a useful range of displacements (>50 nm) while achieving very high position resolution. The passive nature of this technique ensures that the force remains invariant during molecular motions of interest, limited only by the viscous relaxation time of the bead, and not by the often slower response time of any feedback loop. Studying the mechanical unfolding of DNA hairpins, we find that variations in the local stiffness across an optical trap affect the apparent hairpin extension upon unfolding, due to compliance effects, as well as the unfolding rate at equilibrium, due to changes in the effective energy landscape. By adjusting the trap stiffness appropriately, we can therefore modulate the rates of molecular motions, allowing fast transitions to be slowed down to more easily measured timescales.

EXAMPLE 3

Sequencing a DNA Oligonucleotide

Stalled complexes and avidin-coated 600 nm-diameter polystyrene beads were prepared as described by Neuman et al. (2003) Cell 115, 437-447. Polyclonal anti-digoxigenin antibody was covalently attached to carboxylated 730-nm diameter polystyrene beads (Bangs Labs) via an EDC/Sulfo-NHS coupled reaction. RNAP was stalled 29 base pairs after the T7A1 promoter on a template derived from the rpoB gene of *E. coli*.

A bead-RNAP-DNA-bead dumbbell of ~6000 bp total double stranded DNA was constructed by binding a small 600 nm diameter polystyrene bead to a biotin tag located on the β' subunit of a stalled *E. coli* RNAP transcription elongation complex, and a larger 730-nm-diameter bead to the downstream end of the DNA template using a digoxygenin antibody to couple to a digoxygenin molecule incorporated into the 5' end of the DNA.

Figure 3:
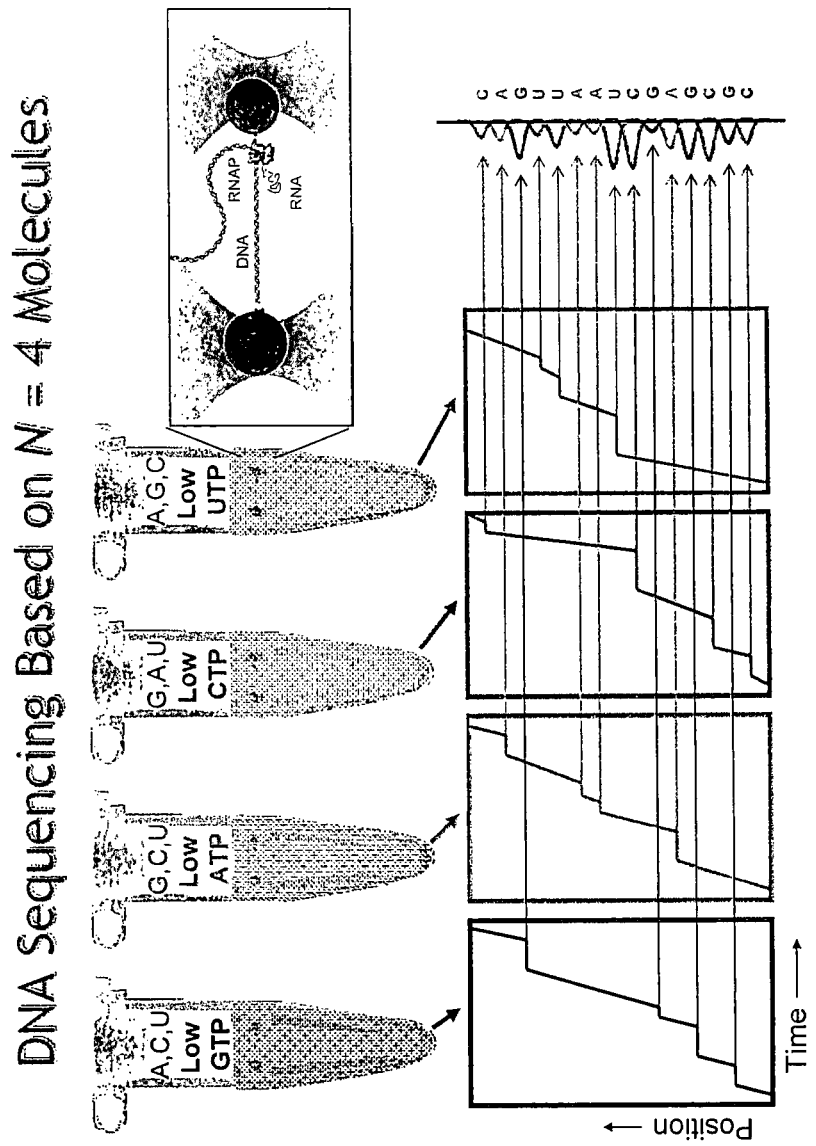
FIG. 3 schematically describes the concept underlying specific embodiment of the invention described. Four single molecules of DNA are measured in four reaction mixtures, each with a different rate-limiting species of rNTP. The aligned pause patterns of the E. coli RNA polymerase are shown schematically below for each molecule. The positions in which these pauses occur uniquely determine the sequence (SEQ ID NO: 1) of the transcribed DNA.
Figure 4:
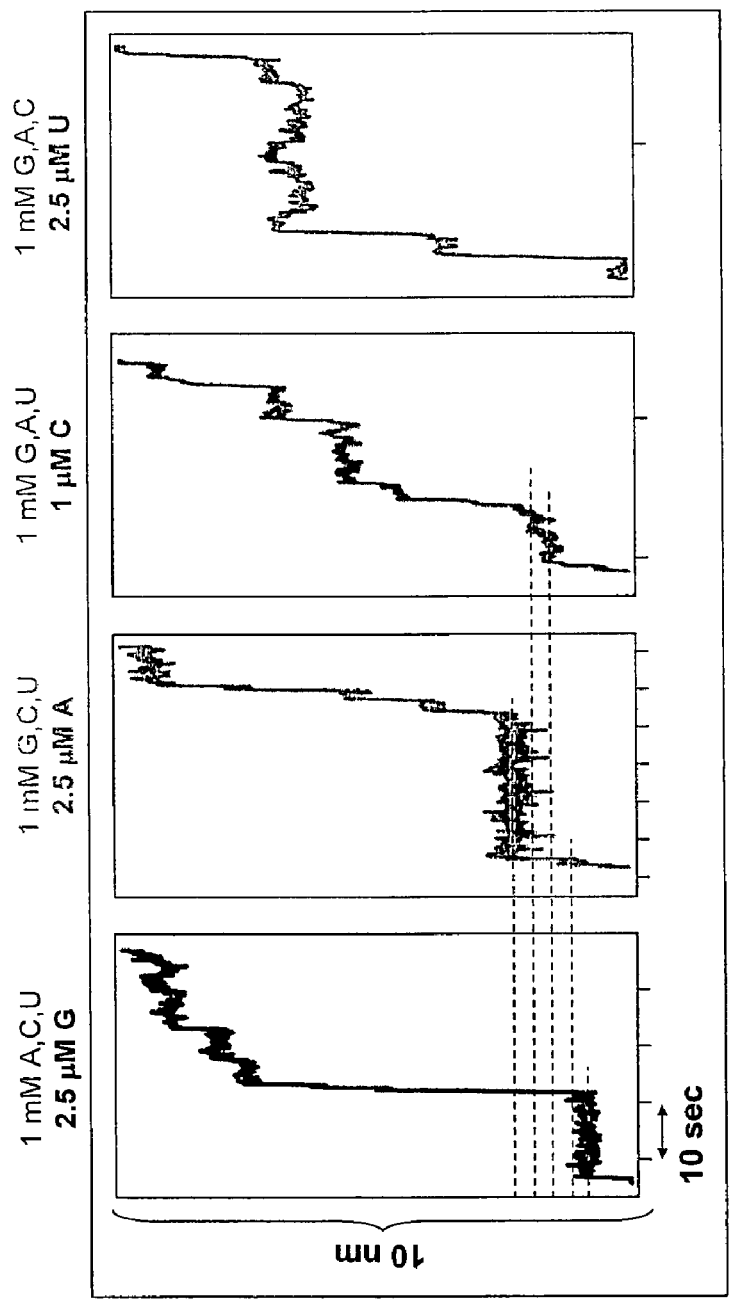
FIG. 4 shows four separate records of ~10 nm of transcription. These records have been aligned using upstream and downstream sequence information to be in register to better than one basepair. Clear pauses are observed corresponding to the positions of the template position of the limiting nucleotide species in each of the traces.

Each of the two beads of the dumbbell was held in a separate optical trap as described in Example 1, 1 μm above the coverglass surface. Transcription along the DNA template was recorded by monitoring the position of the RNAP conjugated bead, held in a passive optical force clamp. All experiments were performed in transcription buffer (50 mM HEPES, pH 8.0, 130 mM KCl, 4 mM MgCl$_2$, 0.1 mM EDTA, 0.1 mM DTT) in the presence of 1 mM NTPs for the non-rate limiting nucleotides, and between 2.5 to 1 μM for the rate limiting nucleotides; and an oxygen scavenging system consisting of β-d glucose, catalase and glucose oxidase as described by Neuman et al. (2003) Cell 115, 437-447 at 22±5° C. Four records of transcription were acquired, with each record taken in buffer with a concentration of one NTP was rate limiting, as shown in FIG. 3 and FIG. 4.

The contour length of the downstream DNA was computed from the measured position of the 600-nm-diameter bead, with no elastic compliance corrections because of the passive, all-optical force-clamping condition. Transcriptional pauses upstream and downstream of a 10 nm segment to be sequenced were used to align the four traces absolutely on the template DNA sequence. This alignment was accomplished to within 2 nm by eye, and to within one base by a cross-correlation algorithm. Briefly, this algorithm cross correlates the expected position of pauses based on the template sequence with the actual observed pauses. This algorithm allowed for small stretch factors and shift factors (up to 10%) on each segment of transcription between updates of the optical force clamp (20 nm segments) in order to maximize alignment by negating the effects of bead variation, and template length variation (as the average rise per base is 3.4±0.34 Angstroms). Final alignment was made by shifting traces very slightly to minimize mutual overlap of position histograms, and minimize overall ambiguity.

Figure 2:
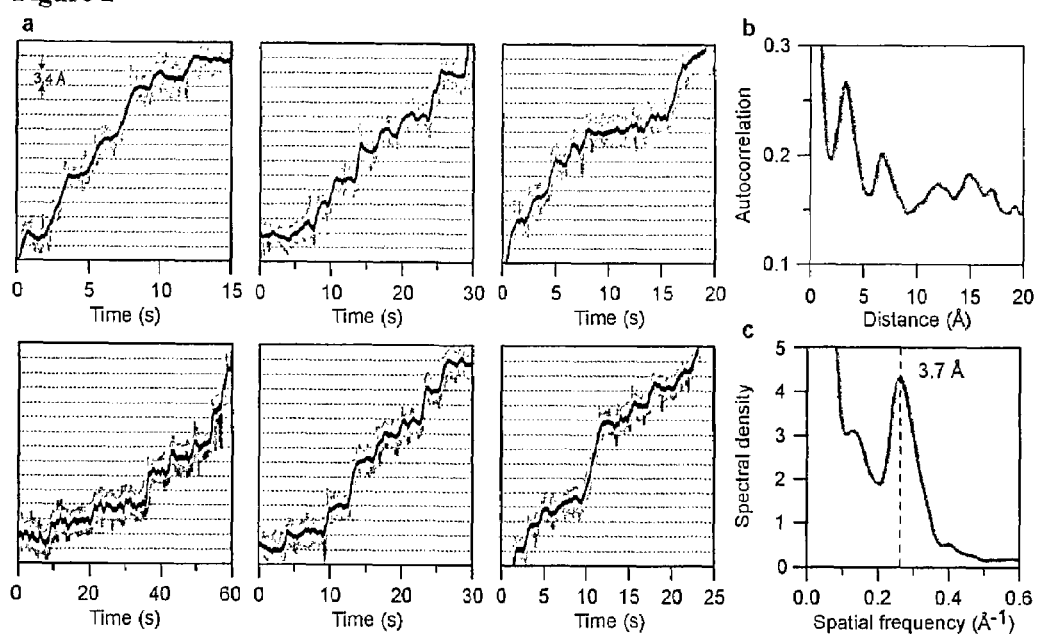
FIG. 2. RNAP moves in discrete steps. a, Representative records for single molecules of RNAP transcribing at $[NTP]_{eq}$ under 18 pN of assisting load, median-filtered at 50 ms (pink) and 750 ms (black). Horizontal lines (dotted) are spaced at 3.4 Å intervals. b, The average autocorrelation function derived from position histograms (N=37) exhibits periodicity at multiples of the step size. c, The power spectrum of b shows a peak at the dominant spatial frequency, corresponding to the inverse of the fundamental step size, 3.7±0.6 Å.

Aligned data from each of the four reactions are shown in FIG. 2 over a segment of the DNA template to be sequenced. These position vs. time traces were histogrammed to generate dwell-time histograms. These traces were slightly attenuated, normalized, and then base assignments were made. Base assignment was performed by first calling unique peaks that occur in a 3.4 Angstrom expected base window; then resolving peak conflicts by assigning peaks to the nearest unassigned base window; and finally calling the highest traces in the center of the expected base window. As shown in FIG. 3, the method provided a high degree of accuracy (29 bases out of 30) in sequencing, using only 4 DNA molecules.

EXAMPLE 4

Single-Molecule, Motion-Based DNA Sequencing using RNA Polymerase

Traditional, dideoxy-based ('Sanger') sequencing of DNA is remarkably reliable and robust. However, the quest for more rapid, economical ways to sequence genomes has driven interest in alternative approaches. Methods capable of sequencing single DNA molecules represent the logical endpoint of miniaturization, leading to the maximum extraction of information from a minimum of material.

Here we report a novel method for sequencing that relies upon resolving the motion of a processive nucleic acid enzyme. We employed a newly-developed assay for transcription by single molecules of *E. coli* RNA polymerase (RNAP) in which a pair of optical traps levitates two polystyrene beads: one attached to the RNAP enzyme, and the other to the distal end of a DNA template. Transcriptional motion of RNAP along the template changes the length of the DNA tether joining the two beads, leading to displacements that can be registered with angstrom-level precision, affording single-base-pair resolution (see Abbondanzieri et al. (2005) Nature 438, 460). When the transcriptional assay is carried out in a buffer where one of the four nucleoside triphosphates (NTPs) is present at very low concentration, the enzyme will be induced to pause at every DNA position that requires the addition of the limiting nucleotide.

To sequence DNA, the single-molecule assay is repeated four times (on four copies of the target DNA sequence), with each NTP species held rate-limiting in turn, and the template sequence is inferred directly from the ordered sequence of pauses in the set of four transcription records. The success of this enterprise relies on being able to align all four records to within one basepair. To establish subnanometer alignment, we used known sequence information found in the DNA regions flanking the unknown segment to be sequenced, which produces an expected pause pattern. This pattern was used to place the four records in register by a maximum correlation method (Herbert et. al. *Cell* 12 (2006)). The flanking sequences used for alignment provide a common starting point, and play an analogous role to the oligonucleotide primers used in Sanger sequencing.

Figure 6:
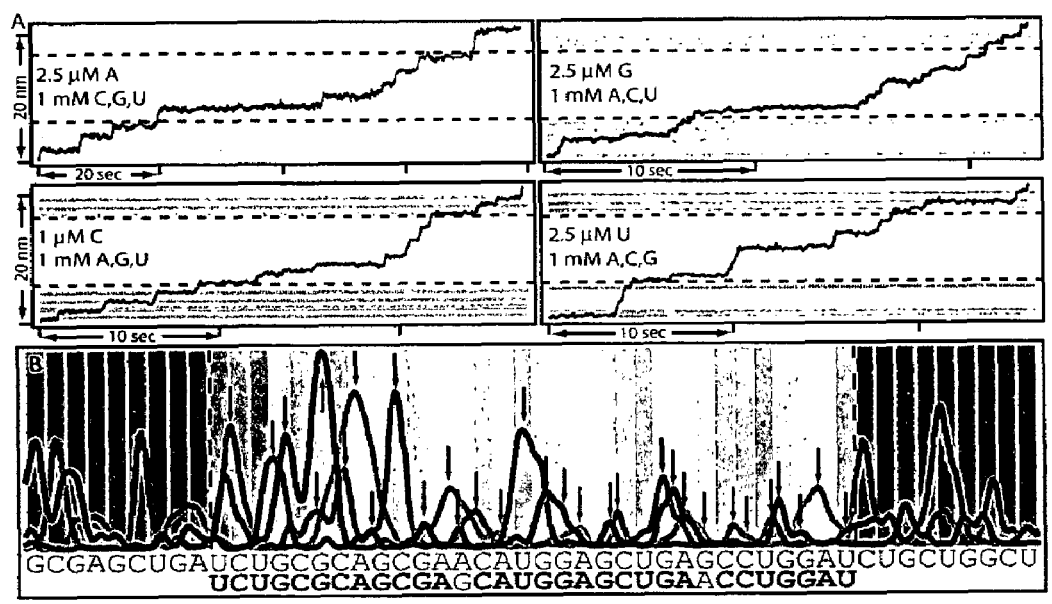
FIG. 6. Motion-based DNA sequencing. (A) Aligned records of transcriptional position vs. time for a single molecule of RNAP under the 4 different limiting nucleotide conditions (ATP, green; CTP, blue; GTP, black; UTP red). Positions of expected pauses used for record alignment (horizontal lines) flank the region to be sequenced (dotted lines). (B) Position histograms for the data in (A), normalized and smoothed. Flanking positions used for alignment (dark vertical bars) and unknown bases to be called (light vertical bars) are shown; bases calls are indicated (arrows). The true sequence of the template (SEQ ID NO: 3) is shown above the inferred sequence (SEQ ID NO: 4), with 30 of 32 correct bases (boldface).

FIG. 6A shows four aligned records. DNA positions from these records were histogrammed, smoothed, and normalized (FIG. 6B). Bases were assigned to every 3.4-Å window (corresponding to the distance spanned by 1 bp) following a simple heuristic. First, if a single histogram peak was detected within one of the windows, it was assigned to the corresponding base. Next, for windows with multiple peaks, the tallest peaks were associated with the nearest unassigned windows. Finally, any remaining windows were assigned to the base with the highest histogram value found at the center of the window. With this scheme, we correctly identified 30 out of 32 bases in a target region based on less than 3 min of net observation time for exactly four molecules (FIG. 6). Greatly improved accuracy can be obtained by combining statistics from multiple single-molecule records and by using more a sophisticated base-calling algorithm, e.g., one based on peak de-convolution or one that incorporates information about the kinetics of sequence-specific elongation of RNA polymerase.

It has proved possible to follow RNAP at the single-molecule level with near-basepair accuracy over templates in excess of 2,000 bp. A factor potentially influencing read length and fidelity may be transcriptional pausing. Approximately 95% of pauses are brief (~1-5 s), sequence-specific, and occur about once every hundred bases, which will not affect the sequencing process. Approximately 5% of pauses exceed 20 s and occur at random positions, about once per thousand bases: these are associated with misincorporation errors. Because such errors are unrelated to any particular sequence, records from multiple molecules may be combined to disambiguate these events from pauses induced by limiting NTPs.

These data demonstrate that the movement of a processive nucleic acid enzyme may be used to extract sequence information directly from DNA.

Materials and Methods

Experimental setup. The dumbbell assay geometry used for single molecule studies of transcription by RNA polymerase (RNAP) is described in detail in Greenleaf et al. (2005) *Phys. Rev. Lett.* 95, 208102. The DNA template used for these experiments was modified slightly from that used in Abbondanzieri et al. (2005) Nature 438, 460 by the inclusion of an additional his terminator sequence at the end of the rpoB gene (see Herbert et al. (2006), supra.) Records were digitally acquired at 2 kHz, decimated with a boxcar filter to a 100 Hz sampling rate, then median filtered at 110 ms.

Record alignment procedure. First, single-molecule records of transcriptional elongation vs. time were roughly aligned, as follows. If the end of a transcription record occurred near a location corresponding to a terminator sequence, then the absolute position was assigned to be that of the terminator. If the end of the record did not occur near a terminator, a contiguous portion of the record devoid of long pauses was used instead to anchor the position: such segments correspond to sequence regions where one of the four NTPs is absent. Because these data were acquired using an optical force clamp, one of the two traps was moved episodically in increments of 20 nm to maintain the position of the detected bead inside the force-clamped region. Log dwell-time histograms of these 20-nm-long segments of continuous transcription were smoothed, then individually aligned on an expected histogram "mask." Outside the alignment region, this mask consisted of unit positive peaks at the positions of the limiting nucleotide and quarter-unit negative peaks were at the positions of non-limiting nucleotides. Inside the alignment region, this mask consisted of quarter-unit positive peaks for every base-window (i.e. the average of all the nucleotide-specific masks), and therefore contained no specific sequence information. The log dwell-time histograms for each segment were autocorrelated against this mask. In this process, the segments were allowed to shift by ±1 nm with respect to the previous segment, and allowed to stretch by ±8%. A stretching parameter allows compensation for the variation in sensitivity in position detection due to size heterogeneity of the polystyrene beads, as well as the sequence-dependent heterogeneity in the linear rise per base for double stranded DNA. A shift parameter allows for compensation of the positional uncertainty generated due to periodic updates of the force clamp. Because of a broad distribution of dwell times at the limiting base, peaks in the dwell-time histogram were used as the primary signal of base identity, using the base-assignment heuristic described in the text. Segments of records used for sequencing analysis were selected from continuous single-molecule records of transcription along templates (~1,000 bp) carrying the known sequence of the rpoB gene from *E. coli*, which codes for the beta subunit of RNA polymerase.

Data analysis. The histograms in FIG. 6 were generated with a 0.1 bp bin width. These histograms were then normalized to have the same integrated area within 44 bp centered on the region to be sequenced. The histograms were then smoothed with a 5-pt boxcar filter followed by a 3-pt binomial filter. Analysis was carried out in Igor Pro 5.01 (Wavemetrics).

What is claimed is:

1. A method of determining the sequence of a polynucleotide, the method comprising:
    (i) contacting a polynucleotide template with a nucleotide-selective, processive enzyme in a reaction mix that is rate-altering for the processive movement of the enzyme for a specified nucleotide;
    (ii) recording the processive movement of the enzyme along the polynucleotide template to provide an enzyme movement trace that differs at the site of the specified nucleotide versus non-specified nucleotides;
    repeating steps (i) and (ii) with reaction conditions that are rate-altering for each nucleotide;
    combining and aligning said enzyme movement traces, wherein the sequence of said polynucleotide template is derived from base specific alteration of movement shown in said enzyme movement traces.

2. The method according to claim 1, wherein said processive enzyme is a polymerase.

3. The method according to claim 2, wherein said reaction mix that is rate-altering for the processive movement of the enzyme for a specified nucleotide comprises a rate limiting concentration of said specified nucleotide.

4. The method according to claim 2, wherein said reaction mix that is rate-altering for the processive movement of the enzyme for a specified nucleotide comprises a rate limiting concentration of all nucleotides other than said specified nucleotide.

5. The method according to claim 2, wherein said reaction mix that is rate-altering for the processive movement of the enzyme for a specified nucleotide comprises a rate altering analog of said specified nucleotide.

6. The method according to claim 1, wherein said polynucleotide is DNA.

7. The method according to claim 1, wherein said polynucleotide is RNA.

8. The method according to claim 1, wherein steps (i) and (ii) are repeated in parallel reactions.

9. The method according to claim 1, wherein steps (i) and (ii) are repeated in serial reactions.

10. The method according to claim 1, wherein each said movement trace is obtained from a single polynucleotide.

11. The method according to claim 1, wherein each said movement trace is obtained from a plurality of polynucleotides.

12. The method according to claim 1, wherein said polynucleotide template is provided in a stretched configuration.

13. The method according to claim 12, wherein a complex of said polynucleotide template and processive enzyme is optically trapped.

14. The method according to claim 12, wherein a complex of said polynucleotide template and processive enzyme is held in a passive optical force clamp.

15. The method according to claim 1, wherein said enzyme movement trace records rotational movement.

16. The method according to claim 1, wherein said enzyme movement trace records translational movement.

17. The method of claim 1, wherein the position of the processive enzyme is tracked fluorescently.

18. The method of claim 1, wherein the position of the processive enzyme is tracked with an atomic force microscope.

19. The method of claim 1, wherein the position of the processive enzyme is tracked using a magnetic tweezers.

20. The method of claim 1, wherein the position of the processive enzyme is tracked using centroid tracking of a fluorescent or non-fluorescent tag.

* * * * *

SEQUENCE LISTING

<160> NUMBER OF SEQ ID NOS: 4

<210> SEQ ID NO 1
<211> LENGTH: 15
<212> TYPE: RNA
<213> ORGANISM: Artificial Sequence
<220> FEATURE:
<223> OTHER INFORMATION: synthetic oligonucletide

<400> SEQUENCE: 1
caguuaaucg agcgc                                                    15

<210> SEQ ID NO 2
<211> LENGTH: 30
<212> TYPE: RNA
<213> ORGANISM: Artificial Sequence
<220> FEATURE:
<223> OTHER INFORMATION: synthetic oligonucletide

<400> SEQUENCE: 2
gucgaccaaa cuaacgaccg ucugagcgca                                    30

<210> SEQ ID NO 3
<211> LENGTH: 50
<212> TYPE: RNA
<213> ORGANISM: Artificial Sequence
<220> FEATURE:
<223> OTHER INFORMATION: synthetic oligonucletide

<400> SEQUENCE: 3
gcgagcugau cugcgcagcg aacauggagc ugagccugga ucugcuggcu              50

<210> SEQ ID NO 4
<211> LENGTH: 32
<212> TYPE: RNA
<213> ORGANISM: Artificial Sequence
<220> FEATURE:
<223> OTHER INFORMATION: synthetic oligonucletide

<400> SEQUENCE: 4
ucugcgcagc gagcauggag cugaaccugg au                                 32